United States Patent [19]

Kreidl et al.

[11] Patent Number: 5,218,119

[45] Date of Patent: Jun. 8, 1993

[54] PROCESS FOR PREPARING THE OCTAHYDRO-INDOLO(2,3-A) QUINOLIZINE DIESTER DERIVATIVES

[75] Inventors: János Kreidl; Mária Farkas née Kirják; Katalin Nógrádi; Ida Deutsch née Juhász, all of Budapest; Judit Mészáros née Brill, deceased, late of Budapest, József Mészáros, Erdélyiné Mészáros Krisztina, heirs; Béla Stefkó, Budapest; György Visky, Budapest; Zsuzsanna Aracs née Tischler, Budapest; Béla Benke, Budapest; Mária Stiller, Budapest; Ferenc Drexler, Budapest, all of Hungary

[73] Assignee: Richter Gedeon Vegyeszeti Gyar Rt., Budapest, Hungary

[21] Appl. No.: 821,326

[22] Filed: Jan. 13, 1992

Related U.S. Application Data

[63] Continuation of Ser. No. 542,486, Jun. 21, 1990, abandoned.

[30] Foreign Application Priority Data

Jun. 21, 1989 [HU] Hungary ............ 3166/89

[51] Int. Cl.$^5$ ............ C07D 471/02
[52] U.S. Cl. ............ 546/70; 546/48
[58] Field of Search ............ 546/70

[56] References Cited

U.S. PATENT DOCUMENTS 4,057,551  11/1977  Szantay et al. ............ 546/70

OTHER PUBLICATIONS

CA: 100 121037j "Octahydroinddo [2,3-Ajquirdizine Mono Esters" by Szantay et al. (1984).
Advanced Organic Chemistry by Jerry March, 3rd Edition, (John-Wiley Sons) P-394, Rxn O-81.

Primary Examiner—Thurman K. Page
Assistant Examiner—Jyothsna Denkat
Attorney, Agent, or Firm—Herbert Dubno; Jonathan Myers

[57] ABSTRACT

The present invention relates to racemic or optically active cis octahydro-indolo [2,3-a] quinolizine diester derivatives.

6 Claims, No Drawings

PROCESS FOR PREPARING THE OCTAHYDRO-INDOLO(2,3-A) QUINOLIZINE DIESTER DERIVATIVES

This is a continuation of co-pending application Ser. No. 07/542,486 filed on Jun. 21, 1990, now abandoned.

FIELD OF THE INVENTION

The present invention relates to novel racemic and optically active cis octahydro-indolo [2,3-a] quinolizine diester derivatives of formula I,

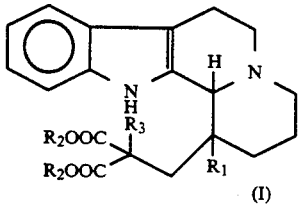

wherein $R_1$ and $R_2$ are independently alkyl having 1 to 4 carbon atoms and $R_3$ represents —$CH_2OH$ group, and optically active cis compounds of formula I, wherein $R_1$ and $R_2$ are the same as defined hereinabove and $R_3$ represents hydrogen atom, and the acid addition salts thereof.

The invention also relates to a new process for the preparation of racemic or optically active cis octahydro-indolo [2,3-a] quinolizine diester derivatives of formula I, wherein $R_1$ and $R_2$ are independently alkyl having 1 to 4 carbon atoms and $R_3$ represents a —$CH_2OH$ group or hydrogen atom, and the acid addition salts thereof.

BACKGROUND OF THE INVENTION

The racemic compounds of formula I wherein $R_3$ stands for hydrogen are known. They are described the first time by Lajos Szabó et al. (Tetrahedron Letters 39, pages 3737-3747). The optically active compounds wherein $R_3$ stands for hydrogen and the racemic and optically active compounds wherein $R_3$ represents —$CH_2OH$ are new.

The racemic or optically active diester derivatives of formula I are very important intermediates for the synthesis of pharmaceutically active compounds of eburnane skeleton such as vincamine and vincamone, and the apovincaminic acid esters, e.g. Cavinton.

SUMMARY OF THE INVENTION

The compounds of formula I are prepared by reducing novel octahydro-indolo 2,3-a tetrahydropyranyl [2,3-c] quinolizine derivatives of formula II

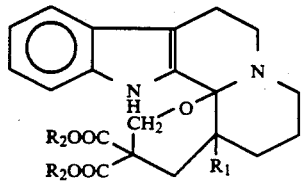

or racemic or optically active hexahydro-indolo [2,3-a] quinolizium salts thereof of formula III,

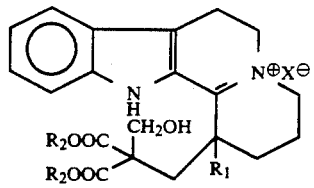

wherein $R_1$ and $R_2$ are the same as defined hereinabove and X represents an acid residue. If desired, the compounds of formula I thus obtained are transformed into acid-addition salts in a known way.

The most important compounds of Formula I are those which are substituted with 1-alkyl group and 12b-H hydrogen in α-position as they can directly be used for the-preparation of the above key-intermediate.

The racemic compounds of Formula I are also useful intermediates, they can be prepared by resolution at any stage of the synthesis.

From the compounds of the present invention the known hydroxyimino-octahydro-indolo[2,3-a] quinolizine derivatives can be prepared by basic treatment followed by nitrosation according to Example 11. From these hydroxyimino derivatives the pharmaceutically active compounds of eburnane skeleton can be prepared in one step according to the process described in Example 12 or 13.

In the above formulae $R_1$ and $R_2$ stand for straight or branched alkyl having 1 to 4 carbon atoms such as methyl, ethyl, n-propyl, i-propyl, n-butyl, i-butyl and t-butyl.

As examples for the acid residue represented by X in formula III organic or inorganic acid residues such as the residues derived from acetic acid, propionic acid, tartaric acid, oxalic acid, hydrochloric acid and phosphoric acid can be mentioned.

The novel starting compounds of formulae II and III can be prepared as follows.

The racemic starting materials can be prepared e.g. by reacting a hexahydro-indolo[2,3-a]quinolizinium diester derivative with formaldehyde in an organic solvent, in the presence of a base (Example 1). The optically active starting materials can be prepared by resolving a novel racemic octahydro-indolo[2,3-a]tetrahydropyranyl[2,3-c] quinolizine derivative (Example 2).

According to the present invention the starting materials can be reduced by catalytic hydrogenation or phase transfer hydrogenation.

The catalytic hydrogenation and the phase transfer hydrogenation can be carried out in the presence of a catalyst either in an aprotic dipolar solvent, e.g. dimethyl formamide or acetone, or in a protic solvent, e.g. ethanol. If the catalytic hydrogenation is carried out in an aprotic dipolar solvent, then optionally an acid, e.g. hydrochloric acid, acetic acid, phosphoric acid, dibenzoyl tartaric acid etc., may also be added to the reaction mixture. Metals, e.g. palladium, platinum, nickel, iron, copper, cobalt, chromium, zinc, molybdenum, tungsten or the oxides thereof, can be used as catalyst.

The catalytic hydrogenation can preferably be carried out in the presence of a catalyst precipitated on the surface of a support. Such a support can be e.g. coal, especially charcoal, silica, the sulfates and carbonates of alkaline earth metals. Most frequently palladium-on-charcoal is used as a catalyst, but the selection of the catalyst always depends on the properties of the compounds to be hydrogenated and on the reaction conditions.

As hydrogen source, hydrogen gas or, in case of phase-transfer hydrogenation, formic acid and the salts thereof, e.g. ammonium formiate, alkaline metal formiates, etc., can be used.

The reaction can be carried out under atmospheric pressure at a temperature of 0° to 100° C., preferably at 20° to 50° C., and the reaction time is about 1 hour.

If the reduction is carried out with the aid of hydrogen gas in an aprotic dipoler solvent, e.g. in dimethyl formamide, optionally in the presence of an acid, then practically a pure compound of formula I wherein $R_3$ stands for —$CH_2OH$ is formed. If the same catalytic hydrogenation is carried out in a protic solvent, e.g. in ethanol, then a mixture of compounds of formula I wherein $R_3$ stands for —$CH_2OH$ and hydrogen, respectively, is formed.

If the same reduction process is carried out at about room temperature, the mixture of the above two compounds is formed. At higher temperatures, e.g. at about 40° to 50° C., mainly the compound of formula I wherein $R_3$ represents hydrogen is formed.

If the reduction is carried out by using formic acid or a salt thereof, e.g. by using ammonium formiate as hydrogen source in a protic solvent such as ethanol, then the compound of formula I wherein $R_3$ stands for hydrogen is formed in practically pure form.

The catalytic hydrogenation can be carried out in any way, the product thus formed, regardless of the substituent represented by $R_3$, is suitable for the preparation of hydroxyimino-octahydro-indolo[2,3-a] quinolizinc derivatives. If desired, the mixture of compounds of formula I can be separated by crystallization.

The saturation reaction is stereoselective which means that the hydrogen atom builds into the position 12b of the molecule in cis position related to the 1-alkyl group, with high (at least 98%) stereoselectivity, i.e. considering the steric position of the 12b-H and 1-alkyl group, practically only cis product is formed. Such a stereospecific saturation is very preferable when pharmaceutically active compounds of eburnane skeleton are prepared as mainly the cis-compounds carrying the 1-alkyl group in α-position lead to pharmaceutically active compounds.

If desired, the compounds thus obtained are isolated in a manner known per se or, if desired, the reduction is carried out in a protic solvent by catalytic hydrogenation and the reaction mixture is used in the next step without isolation of the target compound.

If desired, acid addition salts may be formed in a manner known per se from the compounds of formula I e.g. according to the method described in Example 1.

The invention is further illustrated by the following non-limiting examples.

EXAMPLE 1

(±)-14-diethoxycarbonyl-1-ethyl-1,2,3,4,6,7,12,12b-octahydro-indolo[2,3-a]tetrahydropyranyl[2,3-c]quinolizine (Ia; $R^1$ and $R^2$=ethyl)

55.3 g (0.12 mole) of (±)-1-ethyl-1-(2',2'-diethoxycarbonyl-ethyl)-1,2,3,4,6,7-hexahydro-12H-indolo [2,3] quinolizine-5-ium hydrochloride are suspended in 160 ml of ethanol, then 4.8 g (0.16 mole) of paraformaldehyde and 20.0 ml (0.14 mole) of triethyl amine are added and the reaction mixture is stirred at a temperature of 50° C. for 2 hours. Then the mixture is cooled to a temperature of 0° C. The crystalline suspension is filtered off and washed with cold alcohol. Thus 50.7 g (93%) of the desired compound are obtained.

Melting point: 153°–154° C.

UV (EtOH, $\lambda_{max}$): 296 nm.

EXAMPLE 2

Resolution of (±)-14-diethoxycarbonyl-1-ethyl-1,2,3,4,6,7,12,12b-octahydro-indolo[2,3-a] tetrahydropyranyl[2,3-c]quinolizine (compound of formula III)

To 7.28 g (16 millimoles) of racemic 14-diethoxycarbonyl-1-ethyl-1,2,3,4,6,7,12,12b-octahydro-indolo [2,3-a]tetrahydropyranyl[2,3-c]quinolizine 40.0 ml of acetone are added, then 3.3 g (8.8 millimoles) of (−)-dibenzoyl-d-tartaric acid monohydrate are added to the reaction mixture. The reaction mixture is stirred at room temperature for an hour, then cooled to 10° C. The precipitated crystals are filtered off, washed with acetone and dried. Thus 6.6 g (0.16 millimoles) of (−)-1α-(2'-dicarbethoxy-2'-hydroxymethyl-ethyl)-1β-ethyl-1,2,3,4,6,7-hexahydro-indolo[2,3-a] quinoliziniumdibenzoyl tartarate are obtained. The base content of the product is 55.8% according to perchloric acid titration.

$[\alpha]^{20}_D = -72.5°$ (c=1, dimethyl formamide)

Melting point: 140°–142° C. (decomposition)

Yield: 51.0%.

Then 3 ml of 5% sodium carbonate solution are added to the filtrate and 50 ml of water are added at a temperature of 20° to 25° C. The solution is cooled to 0° C., then washed with 5% acetonic water and dried.

Thus 3.5 g (7.68 millimoles) of (+)-14-diethoxycarbonyl-1α-ethyl-1,2,3,4,6,7,12,12b-octahydro-indolo[2,3-a]tetrahydropyranyl[2,3-c]quinolizine are obtained.

Active ingredient content (on the basis of titration with perchloric acid): 99.8%.

$[\alpha]^{10}_D = +95.7°$ (c=1, dichloromethane).

Melting point: 134°–137° C. (decomposition).

Yield: 48.0%.

EXAMPLE 3

Preparation of (−)-1β-(2'-diethoxycarbonyl-2'-hydroxymethyl-ethyl)-1α-ethyl-1,2,3,4,6,7,12,12b-octahydro-indolo[2,3-a]quinolizine (I; $R_1$ and $R_2$=ethyl, $R_3$=—$CH_2OH$)

30.0 g (0.066 mole) of (+)-14-diethoxycarbonyl-1α-ethyl-1,2,3,4,6,7,12,12bα-octahydro-indolo[2,3-a] tetrahydropyranyl [2,3-c] quinolizine are dissolved in 60 ml of dimethyl formamide, then hydrogenated in the presence of 0.3 g of 10% palladium-on-charcoal catalyst at a temperature of 40° C. under atmospheric pressure. The calculated amount of hydrogen is taken up by the mixture within about 2 hours, then the catalyst is filtered off, 100 ml of water are added to the reaction mixture and the solution is extracted three times with 50 ml of chloroform.

The organic phase is washed with 2×10 ml of water, dried over sodium sulfate and evaporated to dryness in vacuo. The residue is taken up with 50 ml of ethanol and acidified until pH=4 with hydrochloric ethanol. The precipitated crystalline substance is filtered off and washed with ethanol. Thus 29.5 g (91%) of aimed compound are isolated.

Melting point: 215°–218° C.

$[\alpha]^{20}_D = -28.9°$ (c=1, dimethyl formamide).

IR (KBr): 3340 (OH, NH), 730 (CO); 1240 (—OH); 1040 (C—OH) cm$^{-1}$.

MS (M/e, %): 456 (M$^+$:7); 426 (83); 411 (10); 397 (7); 381 (45); 353 (15); 307 (15); 267 (100); 197 (7); 184 (5); 169 (11).

EXAMPLE 4

Preparation of
(−)-1β-(2'-diethoxycarbonyl-2'-hydroxymethyl-ethyl)-1α-ethyl-1,2,3,4,6,7,12,12b-octahydro-indolo [2,3-a]quinolizine hydrochloride (I; R$_1$ and R$_2$=ethyl, R$_3$=—CH$_2$OH)

40.65 g (0.05 mole) of (+)-1β-(2'-diethoxycarbonyl-2'-hydroxymethyl-ethyl)-1α-ethyl-1,2,3,4,6,7-hexahydro-indolo[2,3-a]quinolizinium-d-tartarate are dissolved in 80 ml of dimethyl formamide, then hydrogenated in the presence of 0.4 g of palladium-on-charcoal catalyst under a pressure of 3 atm at a temperature of 20° to 25° C. The calculated amount of hydrogen is taken up within about 1 hour, then the catalyst is filtered off from the solution and 15 ml of aqueous ammonium hydroxide solution and 120 ml of water are added. The mixture is extracted with 3×50 ml of chloroform, the unified organic phases are washed with 2×40 ml of water, dried over sodium sulfate and evaporated under vacuo. The residue is taken up with 65 ml of ethanol and acidified with hydrochloric ethanol until a pH of 4 is reached. The precipitated crystals are filtered off and washed with cold ethanol. Thus 22.0 g (89.5%) of the title product are isolated. The physical characteristics of the product correspond to those of the product obtained in Example 3.

EXAMPLE 5

Preparation of
(−)-1β-(2'-diethoxycarbonyl-ethyl)-1α-ethyl-1,2,3,4,6,7,12,12bα-octahydro-indolo 2,3-a quinolizine (I; R$_1$ and R$_2$=ethyl, R$_3$=H)

To 30.0 g (0.066 mole) of (+)-14-diethoxycarbonyl-1α-ethyl-1,2,3,4,6,7,12,12b-octahydro-indolo [2,3-a] tetrahydropyranyl [2,3-c]quinolizine 150 ml of ethanol, 8.26 g (0.13 mole) of ammonium formiate and 0.3 g of 10% palladium-on-charcoal catalyst are added and the reaction mixture is stirred for 2 hours at a temperature of 40° C. During that time the hydrogenation is completed. Then the catalyst is filtered off, the product is precipitated by slow addition of 150 ml of water, filtered off and dried. Thus 24.5 g (0.057 mole) of the desired product are obtained.

Yield: 87.0%.

Melting point: 75°–78° C.

$[\alpha]^{20}_D = -83°$ (c=1, dichloromethane)

EXAMPLE 6

Preparation of
(−)-1β-(2'-diethoxycarbonyl-2'-hydroxymethyl-ethyl)-1α-ethyl-1,2,3,4,6,7,12,12bα-octahydro[2,3-a]quinolizine (I; R$_1$ and R$_2$=ethyl, R$_3$=—CH$_2$OH) and
(−)-1B-(2'-diethoxycarbonyl-ethyl)-1α-ethyl-1,2,3,4,6,7,12,12bα-octahydro[2,3-a]quinolizine (I; R$_1$ and R$_2$=ethyl, R$_3$=H)

To 30.0 g (0.066 mole) of (+)-14-diethoxycarbonyl-1α-ethyl-1,2,3,4,6,7,12,12b-octahydroindolo [2,3-a] tetrahydropyranyl[2,3-c]quinolizine 150 ml of ethanol, 7.92 g (0.132 moles) of acetic acid and 0.3 g of 10% palladium-on-charcoal are added. The reaction mixture is hydrogenated at a temperature of 25° C. under atmospheric pressure. After 2 hours the reaction is completed, then the catalyst is filtered off, the pH is adjusted to 9 by the addition of water saturated with ammonia, then 150 ml of water are added to the mixture. The precipitated crystals are filtered off and washed with water. Thus 27.57 g of product are obtained which is the mixture of the desired compounds. The mixture comprises 45% of compound of formula I wherein R$^3$=—CH$_2$OH and 55% of the other compound wherein R$^3$ stands for hydrogen, according to HPLC data.

Yield: 95%.

$[\alpha]^{20}_D = -63.5°$ (c=1, dimethyl formamide)

EXAMPLE 7

Preparation of
(+)-1α-(2'-diethoxycarbonyl-2'-hydroxymethyl-ethyl)-1β-ethyl-1,2,3,4,6,7,12,12b-octahydro-indolo[2,3-a]quinolizine hydrochloride (I; R$_1$ and R$_2$=ethyl, R$_3$=—CH$_2$OH)

20.3 g (0.025 mole) of (−)-1α-(2'-diethoxycarbonyl-2'-hydroxymethyl-ethyl)-1β-ethyl-1,2,3,4,6,7-hexahydro-indolo [2,3-a] quinolizinium dibenzol tartarate are dissolved in 40 ml of dimethyl formamide. The hydrogenation and the recovery of the compound are carried out according to Example 3.

Thus 11.4 g (93%) of the aimed product are isolated.

Melting point: 215°–218°.

$[\alpha]^{20}_D = +31.1°$ (c=1, dimethyl formamide).

The spectroscopic data of the product are the same as described in Example 3.

EXAMPLE 8

Preparation of
(−)-1β-(2'-dimethoxycarbonyl-ethyl)-1α-ethyl-1,2,3,4,6,7,12,12bα-octahydro-indolo[2,3-a]quinolizine hydrochloride (I; R$_1$=ethyl, R$_2$=methyl, R$_3$=hydrogen)

To 10.0 g (0.023 mole) of (+)-14-dimethoxycarbonyl-1α-ethyl-1,2,3,4,6,7,12,12bα-octahydroindolo [2,3-a]tetrahydropyranyl[2,3-c]quinolizine 50.0 ml of methanol, 2.9 g (0.046 mole) of ammonium formiate and 0.1 g of 10% palladium-on-charcoal catalyst are added, and the reaction mixture is stirred for 2 hours at a temperature of 40° C. After filtering off the catalyst, the mixture is evaporated to dryness under vacuo. To the evaporation residue 50 ml of dichloromethane and 5% sodium carbonate solution are added until a pH of 9 is reached.

The organic phase is separated, dried over sodium sulfate and filtered off. To the filtrate hydrochloric isopropanol is added slowly until a pH of 3 is reached. The precipitated crystals are filtered off and washed with dichloromethane. Thus 8.95 g (0.0206 mole) of the desired product are obtained.

Yield: 88%.

Melting point: 229°–231° C.

$[\alpha]^{20}_D = -75.8°$ (c=1, dimethyl formamide).

EXAMPLE 9

Preparation of
(±)-(2'-dimethoxycarbonyl-ethyl)-1-ethyl-
1,2,3,4,6,7,12,12b-octahydro-indolo[2,3-a]quinolizine
hydrochloride ($R_3 = H$)

To 10 g (0.023 mole) of 14-dimethoxycarbonyl-1-ethyl-1,2,3,4,6,7,12,12b-octahydro-indolo[2,3-a] tetrahydropyranyl[2,3-c]quinolizine 50 ml of methanol, 2.8 g (0.046 mole) of acetic acid and 0.1 g of 10% palladium-on-charcoal catalyst are added, and the reaction mixture is hydrogenated at a temperature of 55° C. under atmospheric pressure.

The reaction mixture is worked up after the reaction is completed according to Example 8. Thus 9.12 g (0.021 mole) of the aimed product are obtained.

Yield: 92.0%.

Melting point: 236°-238° C.

IR (KBr): 3340 cm$^{-1}$ (indole NH), 1760, 1740 cm$^{-1}$ ($\nu$CO), 2700-2400 cm$^{-1}$ (NH), 1280, 1260 cm$^{-1}$ ($\nu$C—O—C).

EXAMPLE 10

Preparation of
(−)-1$\beta$-(2'-dimethoxycarbonyl-2'-hydroxymethyl-ethyl)-1$\alpha$-ethyl-1,2,3,4,6,7,12,12b-octahydroindolo[2,3-a]quinolizine hydrochloride (I; $R_2$=ethyl, $R_2$=methyl, $R_3$=-CH$_2$OH)

28.1 g (0.066 mole) of (+)-14-dimethoxycarbonyl-1$\alpha$-ethyl-1,2,3,4,6,7,12,12b-octahydro-indolo[2,3-a] tetrahydropyranyl [2,3-c] quinolizine are dissolved in 70 ml of dimethyl formamide, then 2.1 g (0.022 mole) of phosphoric acid are added and the mixture is hydrogenated in the presence of 0.3 g of 10% palladium-on-charcoal catalyst at a temperature of 40° C. under atmospheric pressure. The hydrogenation is completed within 2 hours. Then the catalyst is filtered off. To the filtrate 100 ml of water are added and the pH is adjusted to 9 with concentrated ammonia solution, and the solution is extracted with 3×50 ml of chloroform. The unified organic phases are dried over sodium sulfate, filtered off, then evaporated to dryness under vacuo. To the residue 50 ml of methanol are added and the pH is adjusted to 3 with hydrochloric isopropanol. The precipitated crystals are filtered off and washed with methanol. Thus 28.0 g (0.0603 mole) of the desired compound are obtained.

Yield: 91.5%.

Melting point: 211°-213° C.

$[\alpha]^{20}_D = -30.8°$ (c=1, dimethyl formamide)

EXAMPLE 11

Preparation of
(−)-1$\beta$-[(2'-ethoxycarbonyl-2'-hydroxyimino)ethyl]-
1$\alpha$-ethyl-1,2,3,4,6,7,12,12a-octahydro-indolo[2,3-a]quinolizine hydrochloride To 4.56 g (10 millimoles) of (−)-1$\beta$-(2'-diethoxycarbonyl-2'-hydroxymethyl-ethyl)-1$\beta$-ethyl-1,2,3,4,6,7,12,12b$\beta$-octahydro[2,3a]quinolizine 30 ml of ethanol and 0.56 g (10 millimoles) of potassium hydroxide dissolved in 3 ml of water are added and the reaction mixture is stirred for 1 hour at a temperature of 20 to 25° C. Then ethanol is distilled off under vacuum, and 20 ml of acetic acid and 1.38 g (20 millimoles) of sodium nitrite dissolved in 3 ml of water are added at a temperature of 10° to 15° C. The reaction mixture is kept at this temperature for 2 hours, then cooled below 10° C. and 12 ml of 18% hydrochloric acid are added and the product is precipitated. The substance thus obtained is filtered off, washed with water and dried. Thus 3.44 g (8.2 millimoles) of the desired product are obtained.

Yield: 82%.

Melting point: 257°-260° C.

$[\alpha]^{20}_D = -61°$ (c=1, dimethyl formamide)

EXAMPLE 12

Preparation of (+)cis-apovincaminic acid ethylester 4.75 g (0.025 mole) of p-toluene sulfonic acid monohydrate are dried with toluene at reflux temperature under atmospheric pressure in a flask equipped with a Marcusson distiller, then the amount of toluene is supplemented to 70 ml and 4.2 g (0.01 mole) of (−)-1$\beta$-[(2'-ethoxycarbonyl-2'-hydroxyimino)-ethyl]-1$\alpha$-ethyl-1,2,3,4,6,7,12,12a-octahydro-indolo[2,3-a]quinolizine hydrochloride are added. Then the reaction mixture is refluxed for 1.5 hours, thereafter cooled to room temperature and 30 ml of water are added. The pH of the mixture is set to 9 with aqueous ammonium hydroxide solution. After separation the toluene phase is dried, clarified with charcoal, filtered off and the filtrate is evaporated under vacuum until an oily substance is obtained. The evaporation residue is boiled with 5 ml of ethanol, the precipitated substance is filtered off at 5° C. and dried. Thus 3.14 g of the desired product are obtained.

Yield: 90%.

Melting point: 148°-151° C.

$[\alpha]^{20}_D = +147°$ (c=1, chloroform).

EXAMPLE 13

Preparation of (−) eburnamonine (3$\alpha$,16$\alpha$)

Air is led through a mixture of 3.71 g (0.01 mole) of (−)-1$\alpha$-ethyl-1$\beta$-(2'-methoxycarbonyl-2'-hydroxyimino-ethyl)-1,2,3,4,6,7,12,12a$\alpha$-octahydro-indolo[2,3-a] quinolizine, 50 ml water and 2.0 g (0.05 mole) of solid sodium hydroxide at a temperature of 92° to 96° C. for 1.5 hours under stirring. Then the reaction mixture is cooled to room temperature and 7.4 g (0.075 mole) of 37% aqueous hydrochloric acid solution are added and the mixture is stirred for 1.5 hours at a temperature of 95° to 100° C. Thereafter the reaction mixture is cooled to room temperature, 30.0 ml of dichloromethane are added, then the pH of the mixture is adjusted to 9 by adding concentrated aqueous ammonium hydroxide solution. The phases are separated, the aqueous phase is extracted with 2×5.0 ml of dichloromethane, the organic phases are unified, dried over solid anhydrous sodium sulfate and then filtered off. The solvent of the filtrate is changed to 6.0 ml of methanol by atmospheric distillation. Then the reaction mixture is cooled to a temperature of 0° C.; the precipitaned substance is filtered off, washed with a small amount of cooled methanol and dried. Thus 2.83 g of the desired product are obtained.

Yield: 96.5%.

Melting point: 176.5°-177.5° C.

$[\alpha]^{20}_D = -94.9°$ C. (c=1, chloroform).

Substance content: 99.2% (according to HPLC analysis).

We claim:

1. A process for the preparation of a compound of the Formula (Ia)

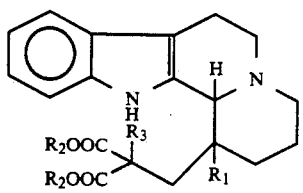

wherein
R₁ and R₂ are independently $C_1$ to $C_4$ alkyl and R₃ is —CH₂OH, wherein the R₁ in the 1-position and the hydrogen in the 12b-position are selectively both in the alpha-position, cis to one another with at least 98% stereoselectivity, which comprises the following steps:
(a) catalytically hydrogenating a compound of the Formula (II)

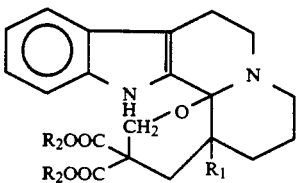

with hydrogen gas at a temperature of 20° to 40° C. in dimethyl formamide.

2. The process for the selective preparation of the compound of the Formula (Ia) defined in claim 1 wherein a palladium-on-carbon hydrogenation catalyst is used to hydrogenate the compound of the Formula (II).

3. A process for the selective preparation of a mixture of compounds of the Formula (I)

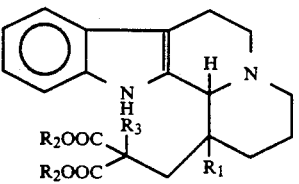

wherein
R₁ and R₂ are each independently $C_1$ to $C_4$ alkyl; and R₃ is hydrogen or —CH₂OH, wherein the R₁ in the 1-position and the hydrogen atom in the 12b-position are selectively both in the alpha-position, cis to one another, with at least 98% stereoselectivity which comprises:
catalytically hydrogenating a compound of the Formula (II)

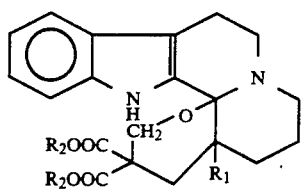

at room temperature in methanol or ethanol with hydrogen gas to yield a mixture of compounds of the Formula (I) wherein R₃ is hydrogen and R₃ is —CH₂OH.

4. The process for the selective preparation of a mixture of compounds of the Formula (I) defined in claim 3 wherein a palladium-on-carbon hydrogenation catalyst is used to hydrogenate the compound of the Formula (II).

5. A process for the selective preparation of a compound of the Formula (Ib)

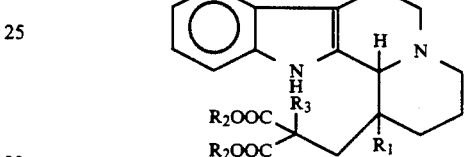

wherein
R₁ and R₂ are each independently $C_1$ to $C_4$ alkyl; and R₃ is hydrogen,
wherein the R₁ in the 1-position and the hydrogen atom in the 12b-position are selectively both in the alpha-position, cis to one another with at least 98% stereoselectivity, which comprises:
catalytically hydrogenating a compound of the Formula (II)

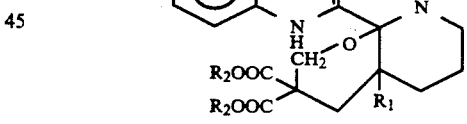

at 40° to 50° C. with hydrogen gas, formic acid or ammonium formate in methanol or ethanol.

6. The process for the selective preparation of a compound of the Formula (Ib) defined in claim 5 wherein a palladium-on-carbon hydrogenation catalyst is used to hydrogenate the compound of the Formula (II).

* * * * *